(12) United States Patent
Clark et al.

(10) Patent No.: US 10,695,030 B2
(45) Date of Patent: Jun. 30, 2020

(54) ULTRASOUND ELASTOGRAPHY SYSTEM AND METHOD

(71) Applicant: KONINKLIJKE PHILIPS N.V., Eindhoven (NL)

(72) Inventors: David W. Clark, Derry, NH (US); Elizabeth Brunelle, Portsmouth, NH (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1045 days.

(21) Appl. No.: 14/344,329

(22) PCT Filed: Sep. 21, 2012

(86) PCT No.: PCT/IB2012/055015
§ 371 (c)(1),
(2) Date: Mar. 12, 2014

(87) PCT Pub. No.: WO2013/050899
PCT Pub. Date: Apr. 11, 2013

(65) Prior Publication Data
US 2014/0350398 A1   Nov. 27, 2014

Related U.S. Application Data

(60) Provisional application No. 61/539,599, filed on Sep. 27, 2011.

(51) Int. Cl.
*A61B 8/00* (2006.01)
*A61B 8/08* (2006.01)
(Continued)

(52) U.S. Cl.
CPC ............ *A61B 8/485* (2013.01); *A61B 5/0053* (2013.01); *A61B 5/7221* (2013.01); *A61B 8/463* (2013.01); *A61B 6/5235* (2013.01); *A61B 8/4494* (2013.01)

(58) Field of Classification Search
CPC combination set(s) only.
See application file for complete search history.

(56) References Cited

U.S. PATENT DOCUMENTS 5,474,070 A * 12/1995 Ophir .................. A61B 5/0048
600/437
6,514,204 B2    2/2003 Alam et al.
(Continued)

OTHER PUBLICATIONS

Sensitivity and Strength, Philips Breast Elastography Ultrasound Quick Start Guide, Philips 2010, http://www.healthcare.philips.com/main/products/ultrasound/technologies/elastography.wpd, 6 Pages.
(Continued)

*Primary Examiner* — Joel F Brutus (57) ABSTRACT

The present invention relates to an ultrasound elastography system and method for providing a strain image of an anatomical site. The system comprises a signal processing unit (103) configured to receive a time-varying ultrasound signal from an ultrasound probe (101) having at least one transducer element, to determine axial motion data based on the time-varying ultrasound signal, the axial motion data indicating a relative axial motion between the ultrasound probe and the anatomical site in an axial direction (y), and to determine a lateral variation of the axial motion in a lateral direction (x) based on the axial motion data. The system further comprises a display unit (105) configured to display a strain image (200) of the anatomical site based on strain image data which is determined based on the axial motion data, and to display an indication of lateral variation of a quality of the strain image based on the lateral variation of the axial motion.

10 Claims, 7 Drawing Sheets

222

(51) Int. Cl.
*A61B 5/00* (2006.01)
*A61B 6/00* (2006.01)

(56) References Cited

U.S. PATENT DOCUMENTS

| | | | | |
|---|---|---|---|---|
| 6,558,324 | B1* | 5/2003 | Von Behren | A61B 8/08 |
| | | | | 600/437 |
| 7,331,926 | B2 | 2/2008 | Varghese et al. | |
| 2005/0165309 | A1* | 7/2005 | Varghese | A61B 8/00 |
| | | | | 600/449 |
| 2005/0187470 | A1* | 8/2005 | Kubota | A61B 8/08 |
| | | | | 600/437 |
| 2006/0025682 | A1 | 2/2006 | Vanderby et al. | |
| 2006/0285731 | A1* | 12/2006 | Jiang | A61B 8/08 |
| | | | | 382/128 |
| 2007/0167772 | A1* | 7/2007 | Radulescu | A61B 8/08 |
| | | | | 600/438 |
| 2007/0232916 | A1* | 10/2007 | Waki | A61B 5/6843 |
| | | | | 600/444 |
| 2007/0244390 | A1* | 10/2007 | Matsumura | A61B 8/08 |
| | | | | 600/437 |
| 2009/0275837 | A1 | 11/2009 | Shiina et al. | |
| 2010/0016718 | A1 | 1/2010 | Fan et al. | |
| 2010/0134629 | A1* | 6/2010 | Lindop | A61B 8/08 |
| | | | | 348/163 |
| 2010/0179413 | A1 | 7/2010 | Kadour et al. | |
| 2010/0185090 | A1* | 7/2010 | Suzuki | A61B 8/0858 |
| | | | | 600/443 |
| 2010/0220901 | A1* | 9/2010 | Matsumura | A61B 8/08 |
| | | | | 382/128 |
| 2010/0292572 | A1 | 11/2010 | Hope Simpson et al. | |
| 2011/0306883 | A1* | 12/2011 | Park | A61B 5/0048 |
| | | | | 600/443 |
| 2012/0128223 | A1* | 5/2012 | Rivaz | A61B 8/485 |
| | | | | 382/131 |

OTHER PUBLICATIONS

Lindop et al, "Dynamic Resolution Selection in Ultrasonic Strain Imaging", Ultrasound in Medicine and Biology, vol. 34, No. 5, May 1, 2008, pp. 809-823.

Bu et al, "3D Myocardial Strain Imaging: Improvement of Accuracy and Contrast by Dynamic Grid Interpolation", Ultrasonics Symposium, IEEE, Oct. 1, 2007, pp. 1937-1940.

Prager et al, "Deconvolution and Elastography Based on Three-Dimensional Ultrasound" Ultrasonics Symposium, IEEE Nov. 2, 2008, pp. 548-557.

Konofagou et al, "A New Elastographic Method for Estimation and Imaging of Lateral Displacements, Lateral Strains, Corrected Axial Strains and Poisson's Ratios in Tissues" Ultrasound in Med. & Biol., vol. 24, No. 8, 1998, pp. 1183-1199.

Lubinski et al, "Lateral Displacement Estimation Using Tissue Incompressibility", IEEE Transactions on Ultrasonics, Ferroelectrics, and Frequency Control, vol. 43, No. 2, Mar. 1996, pp. 247-256.

* cited by examiner

ULTRASOUND ELASTOGRAPHY SYSTEM AND METHOD

This application is the U.S. National Phase application under 35 U.S.C. §371 of International Application No. PCT/2012/055015 filed on Sep. 21, 2012 which claims the benefit of U.S. Provisional Patent Application No. 61/539,599 filed on Sep. 27, 2011. These applications are hereby incorporated by reference herein.

FIELD OF THE INVENTION

The present invention relates to an ultrasound elastography system and method for providing a strain image of an anatomical site (e.g. an anatomical site of a patient). The present invention further relates to a computer program for implementing such method.

BACKGROUND OF THE INVENTION

In ultrasound strain elastography an image of relative axial strain, which is associated with tissue stiffness differences, is displayed. This strain image (also called elastogram), can for example help to distinguish lesion malignancy. An estimation of axial strain requires some axial compression (or de-compression) in the form of a relative axial motion between transducer element(s) of an ultrasound probe and the anatomical site (e.g. a patient's (deeper) tissues). Such compression can be provided by the weight of the ultrasound probe and/or by physical pressure applied by the user of the system (e.g. medical staff or a doctor) and/or by internal patient motion due to heartbeat or breathing. A sensitive elastography system can require very little motion (e.g. a relative axial motion in the order of 10 μm). More compression can tend to improve the strain image quality, until degrading effects such as de-correlation, blurring or misregistration can become dominant (e.g. around a relative axial motion of about 1 mm). Because the required (slight) relative axial motion for ultrasound elastography may approach the limit of the user's physical perception and/or because it may affect the quality of the strain image, an elastography system can be able to display an indication of the quality of the strain image. This indication can for example be a (non-quantitative) bar graph next to the strain image.

An exemplary elastography system displaying such bar graph is the Philips iU22 system. For example, the brochure "Sensitivity and strength, Philips Breast Elastography Ultrasound Quick Start Guide, Philips, 2010" (e.g. currently to be found at http://www.healthcare.philips.com/main/products/ultrasound/technologies/elastography.wpd), which is a quick start guide providing a brief overview of the Philips iU22 breast elastography system, discloses that a real-time compression feedback bar is displayed next to the strain image. This on-screen indicator provides the user with real-time feedback on the appropriate amount of deformation for the elastogram. The system computes the level of resulting tissue deformation and displays it as a green and grey bar to indicate appropriate (green) and inappropriate (grey) tissue deformation for a quality elastogram.

There is a need to further improve such elastography system.

SUMMARY OF THE INVENTION

It is an object of the present invention to provide an improved ultrasound elastography system and method. It is a further object of the present invention to provide a computer program for implementing such method.

In a first aspect of the present invention an ultrasound elastography system for providing a strain image of an anatomical site is presented. The system comprises a signal processing unit configured to receive a time-varying ultrasound signal from an ultrasound probe having at least one transducer element, to determine axial motion data based on the time-varying ultrasound signal, the axial motion data indicating a relative axial motion between the ultrasound probe and the anatomical site in an axial direction, and to determine a lateral variation of the axial motion in a lateral direction based on the axial motion data. The system further comprises a display unit configured to display a strain image of the anatomical site based on strain image data which is determined based on the axial motion data, and to display an indication of lateral variation of a quality of the strain image based on the lateral variation of the axial motion.

In a further aspect of the present invention an ultrasound elastography method for providing a strain image of an anatomical site is presented. The method comprises receiving a time-varying ultrasound signal from an ultrasound probe having at least one transducer element, determining axial motion data based on the time-varying ultrasound signal, the axial motion data indicating a relative axial motion between the ultrasound probe and the anatomical site in an axial direction, determining a lateral variation of the axial motion in a lateral direction based on the axial motion data, displaying a strain image of the anatomical site based on strain image data which is determined based on the axial motion data, and displaying an indication of lateral variation of a quality of the strain image based on the lateral variation of the axial motion.

In a further aspect of the present invention a computer program is presented comprising program code means for causing a computer to carry out the steps of such method when said computer program is carried out on the computer.

The basic idea of the invention is to determine a lateral variation of axial motion and to display an indication of lateral variation of strain image quality based on this lateral variation of the axial motion. The lateral direction is orthogonal to the axial direction. In particular, the axial direction can be the depth direction (e.g. orthogonal to the skin of the patient) and/or the direction in which the transducer element(s) transmits ultrasound waves. The or each transducer element is configured to transmit and/or receive ultrasound waves. Relative axial motion can be regarded as relative axial displacement between the ultrasound probe (or transducer element(s)) and the anatomical site from one point of time to another point of time. Relative axial motion can thus be determined from a time-varying ultrasound echo signal. Each axial line of an ultrasound image can be constructed from ultrasound echo (intensity and/or phase) data resulting from echo signals received at the transducer element(s) from progressively deeper depths following each transmit pulse of at least one transmit pulse transmitted by the transducer element(s). In particular, relative axial motion can be determined by comparing the ultrasound echo signals at the same anatomical site (or spatial location) from at least two different transmit pulses (at two different points of time).

Especially when the relative axial motion is very slight and not even deliberate, there can be as much (or even more), lateral tilting and/or rocking as there is overall axial motion. This means that the axial motion can significantly vary across the strain image area. Often this pattern of lateral tilting and/or rocking is not random, but is relatively stable over time, e.g. several seconds, because it depends on the physical arrangement of the user's body and the patient's body. By displaying the indication of lateral variation of the strain image quality the user gets an indication of the lateral variation and may adjust his or her holding and/or motion of the ultrasound probe accordingly. Thus, the user can be guided by the indication to improve the quality of the strain image.

Preferred embodiments of the invention are defined in the dependent claims. It shall be understood that the claimed ultrasound elastography method or computer program has similar and/or identical preferred embodiments as the claimed ultrasound elastography system and as defined in the dependent claims.

In one embodiment the lateral variation of the axial motion is determined by determining, for at least two lateral positions in the lateral direction, an amount of relative axial motion and by comparing the amounts of axial motion. In this embodiment a simple way of determining the lateral variation of the axial motion is provided.

In a variant of this embodiment the display unit is configured to display the indication of the lateral variation of the strain image quality by displaying an indication of the amount of relative axial motion as a function of the lateral position. In this variant the indication of the lateral variation of the strain image quality is directly an indication of the amount of relative axial motion as a function of the lateral position.

In another embodiment the axial motion data is two-dimensional data for a plurality of points each having an axial position and a lateral position, the axial motion data indicating an amount of axial motion for each point of the plurality of points. In this embodiment a two-dimensional strain image can be displayed.

In a variant of this embodiment determining the lateral variation of the axial motion comprises averaging, for each of at least two lateral positions in the lateral direction, the amounts of relative axial motion of the points of the plurality of points which have the respective lateral position. In this variant the axial motion amounts are averaged. Thus, average axial motion as a function of lateral position is provided, which thus shows the lateral variation of axial motion.

In an alternative variant of this embodiment determining the lateral variation of the axial motion comprises averaging, for each of at least two lateral positions in the lateral direction, the axial derivatives of the amounts of relative axial motion of the points of the plurality of points which have the respective lateral position. In this variant the strains (derivatives of axial motion amounts) are averaged. Thus, average strain as a function of lateral position is provided which thus shows the lateral variation of axial motion.

In a further embodiment the indication of strain image quality is a bar graph having a bar. In this embodiment a simple implementation of the stain image quality indication is provided. The indication in form of the bar graph does not need to occupy any additional space on the display compared to a conventional bar graph. It can still be a non-quantitave indication. It can be intuitive enough that very little user training or practice is needed.

In a variant of this embodiment a height of the bar indicates a level of strain image quality. In particular, the height of the bar can indicate the amount of axial motion. In this variant the user can easily be guided by simply watching the height of the bar.

In a further variant a shape of the bar indicates the lateral variation of the strain image quality. In this embodiment an advantageous implementation of an indication of lateral variation of strain image quality is provided. For example, if there is no lateral variation of axial motion (thus the motion is purely axial), the shape of the bar can be rectangular, like a conventional bar graph. If there is lateral variation of the axial motion present, the shape of the bar can change. For example, at least one side (e.g. the top side) of the bar can change. In this way lateral variation can be easily perceived by the user.

In a further variant the shape of the bar is slanted and/or curved when the strain image quality laterally varies. In particular, the shape of the bar can have at least two different heights. In this variant an advantageous implementation for the indication of the lateral variation of strain image quality is provided. If there is lateral variation of the axial motion (e.g. rocking and/or tilting), the shape of the bar (e.g. its top side) becomes slanted and/or curved. In particular, the shape of the bar may become V-shaped when the strain image quality varies. This V-shape may indicate that the lateral variation of the axial motion (e.g. rocking and/or tilting) exceeds the axial motion, so that the axial motion changes direction in the lateral direction (laterally across the image), with an intermediate region having nearly zero axial motion.

In a further embodiment the indication of the lateral variation of the strain image quality is displayed in real-time and/or stored in a memory for later displaying. By displaying the indication in real-time, the user gets immediate feedback about the lateral variation. By storing the indication in memory, the strain image quality can be displayed or reviewed at a later point of time.

In a further embodiment the display unit is further operable to display ultrasound echo intensity image of the anatomical site. The ultrasound echo intensity image can for example be a two-dimensional, three-dimensional or multi-planar ultrasound echo intensity image.

In a variant of this embodiment the ultrasound echo intensity image can be displayed based on echo intensity data which is determined based on the ultrasound signal. In this embodiment the system is not only configured to display a strain image, but also to display a conventional ultrasound echo density image. In one example, the ultrasound echo intensity image and the strain image can be based on the ultrasound echo signal from the same transmit pulse or the same set of transmit pulses. In an alternative example, the ultrasound echo intensity image and the strain image can be based on the ultrasound echo signal from different transmit pulses or different sets of transmit pulses.

In a further embodiment the signal processing unit is configured to determine an elevational variation of the axial motion in an elevation direction based on the axial motion data, and the display unit is configured to display an indication of elevational variation of strain image quality based on the elevational variation of the axial motion. In this embodiment, not only a lateral variation of the axial motion is provided, but additionally also an elevational variation of the axial motion. Thus, the variation of the axial motion in two different dimensions is provided. In general, this could be extended to more than two directions, which would then not be orthogonal to each other In a further embodiment, the system comprises the ultrasound probe having the at least one transducer element. In this embodiment the ultrasound probe is thus part of the system. For example, it can be (directly) connected to the signal processing unit.

In a variant of this embodiment the ultrasound probe has a plurality of transducer elements. The plurality of transducer elements can in particular be arranged in a (one-dimensional) row or a (two-dimensional) array. In this way a two-dimensional or multi-planar or three-dimensional image can be provided.

BRIEF DESCRIPTION OF THE DRAWINGS

These and other aspects of the invention will be apparent from and elucidated with reference to the embodiment(s) described hereinafter. In the following drawings

DETAILED DESCRIPTION OF THE INVENTION

Figure 1:
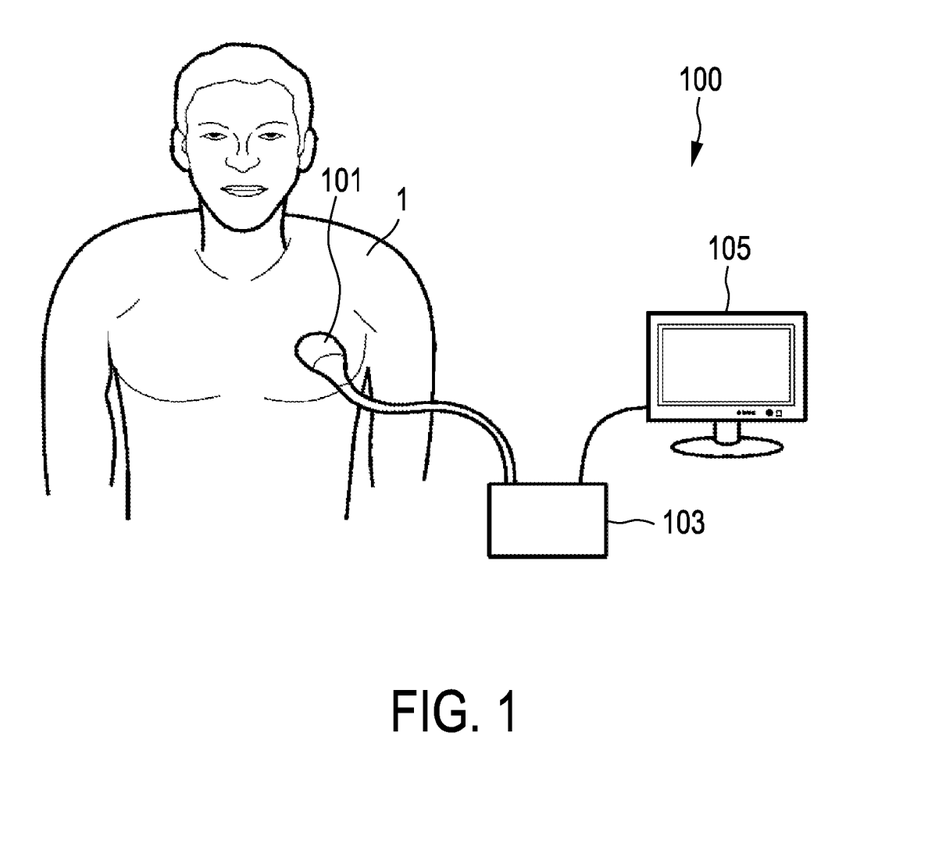
FIG. 1 shows a schematic block diagram of an ultrasound elastography system according to an embodiment.

FIG. 1 shows a schematic block diagram of an ultrasound elastography system 100 according to an embodiment, in particular a medical ultrasound imaging system. The ultrasound elastography system 100 comprises an ultrasound probe 101 having a plurality of transducer elements for transmitting and/or receiving ultrasound waves. In one example, the transducer elements can transmit ultrasound waves in form of at least one transmit pulse of a specific pulse duration (in particular a plurality of subsequent transmit pulses). In an alternative example, the transducer elements can transmit ultrasound waves in form of continuous wave (CW), although that is not typically used for imaging. The transducer elements can for example be arranged in a (one-dimensional) row (e.g. for providing a two-dimensional image) or in a (two-dimensional) array (e.g. for providing a multi-planar or three-dimensional image). The ultrasound probe 101 may be handheld by the user of the system (e.g. medical staff or a doctor). The ultrasound probe 101 is applied to the body of a patient 1 for providing a strain image of an anatomical site in the patient 1.

The ultrasound elastography system 100 further comprises a signal processing unit 103. The signal processing unit 103 may for example include analog or digital electronic circuits, a processor, microprocessor or the like. The signal processing unit 103 is connected to the ultrasound probe 101. The signal processing unit 103 is configured to receive a time varying ultrasound signal from the ultrasound probe 101, in particular from the transducer elements receiving the ultrasound waves. In this context time-varying means that the ultrasound signal is received over time. More particularly, an echo from a single transmit pulse is spread over time corresponding to progressively deeper depths, and echoes (ultrasound echo signal) are received from multiple transmit pulses. The signal processing unit 103 is configured to determine axial motion data based on the time-varying ultrasound signal. The axial motion data indicates a relative axial motion between the ultrasound probe 101 (or its transducer elements) and the anatomical site in an axial direction. In particular, relative axial motion can be determined by comparing the ultrasound echo signals at the same anatomical site (or spatial location) from at least two different transmit pulses (at two different points of time). For strain elastography, the axial direction is usually the depth direction (aligned with the centerline of the ultrasound probe), for example orthogonal to the skin of the patient 1 when the ultrasound probe 101 is externally applied to the skin. In general, the axial direction is the direction in which the ultrasound transducer elements transmit the ultrasound waves. Alternatively, the ultrasound waves or beams can be steered at an angle with respect to the depth direction or centerline of the ultrasound probe (e.g. using a beam former). Further alternatively, the transducer elements may be arranged in a curve so as to transmit ultrasound waves at various angles with respect to the depth direction or centerline of the ultrasound probe. For these more generalized cases of axial direction, lateral direction can be understood to mean across the strain image (across the set of axial ultrasound lines).

Relative axial motion can be regarded as relative axial displacement between the ultrasound probe and the anatomical site, from the ultrasound echo signal from one transmit pulse to the corresponding ultrasound echo signal from another transmit pulse in the same direction(e.g. echoes at two different points of time). The relative axial motion results from some relative axial compression (or decompression) between the ultrasound probe and the anatomical site. The compression can be provided by the weight of the ultrasound probe 1 and/or by physical pressure applied by the user of the system. The signal processing unit 103 can be configured to determine strain image data based on the axial motion data. Strain image data can in particular be determined by determining the axial derivative of the axial motion data. Thus, strain can be regarded as the axial derivative of axial motion. This can be an incremental strain over each of a plurality of short image time intervals. Alternatively, these incremental strains could also be accumulated to yield a total strain.

The ultrasound elastography system 100 further comprises a display 105. The display 105 is connected to the signal processing unit 103 for receiving image data from the signal processing unit 103. The display 105 is configured to display a strain image of the anatomical site based on the determined strain image data.

Figure 2:
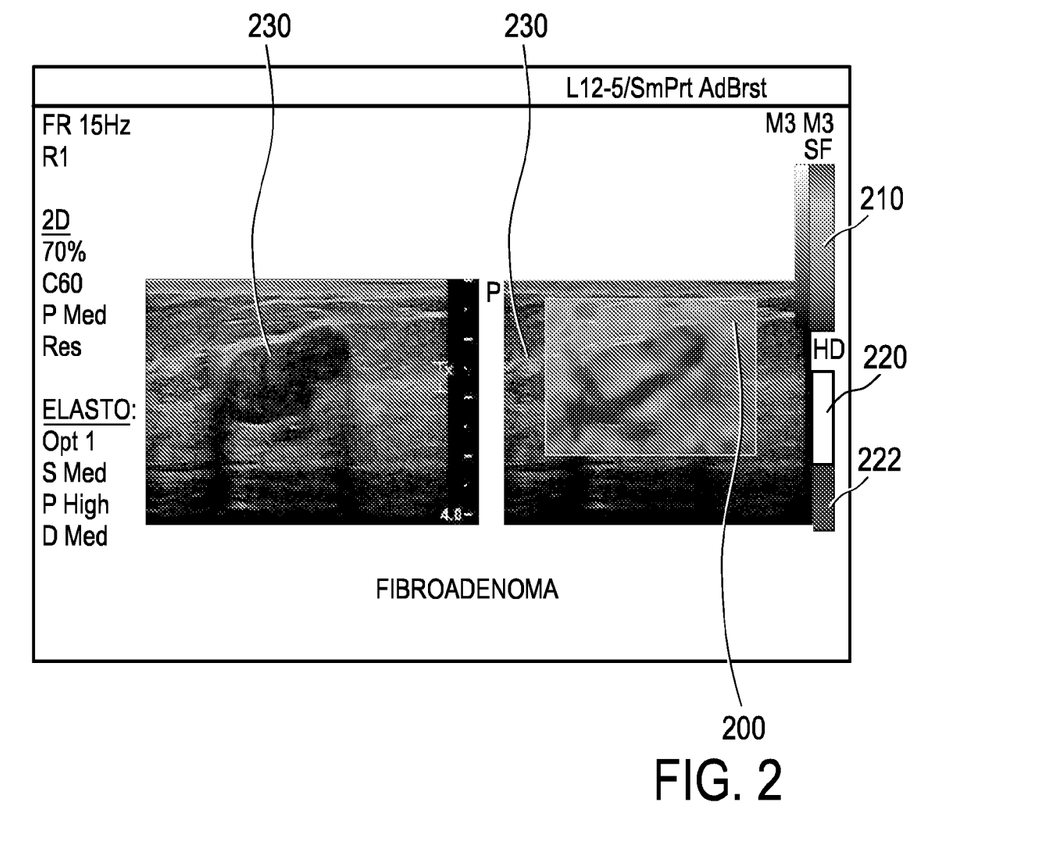
FIG. 2 shows an exemplary image displayed on a display of an ultrasound elastography system according to an embodiment.

FIG. 2 shows an exemplary image displayed by a display of an ultrasound elastography system according to an embodiment. The image can in particular be displayed by the display 105 of the ultrasound system 100 as explained with reference to FIG. 1. The displayed image comprises a two-dimensional ultrasound echo intensity image 230 of the anatomical site. The echo intensity image of FIG. 2 is a two-dimensional gray scale image. The ultrasound echo intensity image 230 can be displayed based on echo intensity data which is determined based on the ultrasound signal. Thus, the signal processing unit 103 can further be configured to determine echo intensity data based on the ultrasound signal. In the image of FIG. 2 one echo intensity image 230 is displayed on the left side. The same echo intensity image 230 is displayed on the right side, but additionally a strain image 200 is overlaid on the strain image 230. The strain image 200 is overlaid on the echo intensity image 230 in form of a window. The strain image 200 can be displayed using a color scale, thus a variety of colors (e.g. a color spectrum ranging from blue to red). A legend 210 can indicate the color range. Just as an example, the color blue on the bottom of the legend 210 can indicate hard tissue (abbreviated by HD in FIG. 2) and the color red on the top of the legend 210 can indicate soft tissue (abbreviated by SF in FIG. 2). Alternatively, the strain image 200 can be displayed using a gray scale.

The signal processing unit 103 is further configured to determine a lateral variation of the axial motion in a lateral direction based on the axial motion data, and the display unit 105 is further configured to display an indication of lateral variation of a quality of the strain image 200 based on the lateral variation of the axial motion. For strain elastography, the lateral direction is usually orthogonal to the axial direction. However, as mentioned above, for more generalized cases of axial direction (e.g. steering of ultrasound waves at an angle or arrangement of transducer elements in a curve), lateral direction can in general mean across the strain image (across the set of axial ultrasound lines).

By displaying the indication of lateral variation of the strain image quality, the user (e.g. medical staff or a doctor) gets an indication of the lateral variation and may adjust his or her holding of the ultrasound probe 101 accordingly. Thus, the user can be guided by the indication to improve the strain image quality. Alternatively or cumulatively, a later reviewer can interpret the strain image accordingly. In the embodiment of FIG. 2, the indication of strain image quality is a bar graph 220 having a bar 222. The indication of the lateral variation in form of the bar graph 222 is displayed in the vicinity of the strain image 200 (in FIG. 2 right of the strain image 200). The indication of the lateral variation of the strain image quality can be displayed in real time. Alternatively, the indication of the lateral variation of the strain image quality can be stored in a memory for later displaying. The later displaying or reviewing can be performed on the ultrasound system 100 itself or on some other review system.

Figure 2A:
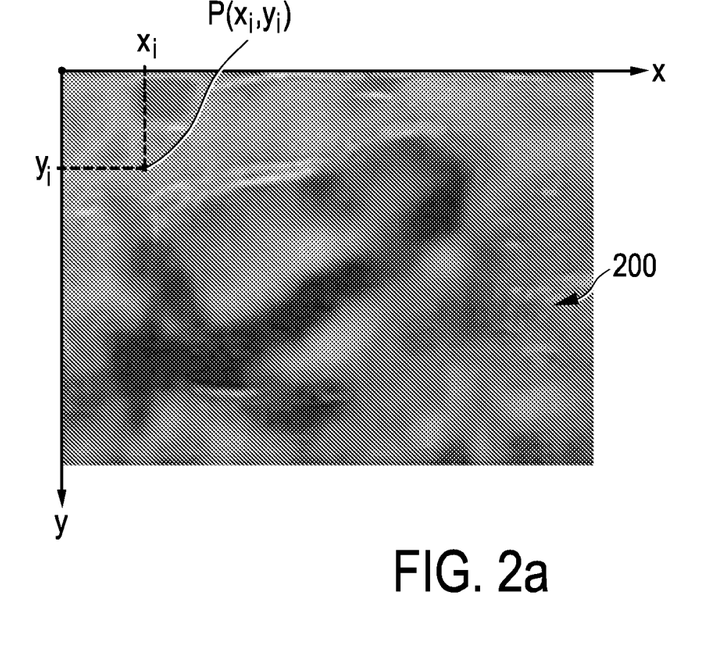
FIG. 2*a* shows an enlarged view of a portion of the image of FIG. 2.

FIG. 2a shows an enlarged view of a portion of the image of FIG. 2. The portion of the image shown in FIG. 2a is the strain image 200 of FIG. 2. The y-axis of the strain image 200 indicates the axial direction and the x-axis of the strain image 200 indicates the lateral direction x. In this case, the axial motion data is two-dimensional data for a plurality of points $P(x_i, y_i)$ each having an axial position $y_i$ and a lateral position $x_i$. The axial motion data indicates an amount of relative axial motion for each point $P(x_i, y_i)$ of the plurality of points. The lateral variation of the axial motion can be determined by determining for at least two lateral positions $x_i$ in the lateral direction x, an amount of relative axial motion and by comparing these amounts of axial motion. For example, a first amount of axial motion can be determined for a first lateral position $x_1$ and a second amount of axial motion can be determined for a second lateral position $x_2$. The first amount of axial motion and the second amount of axial motion can then be compared to determine the lateral variation. The display unit 105 can be configured to display the indication of the lateral variation of the strain image quality by displaying an indication of the amount of axial motion as a function of the lateral position $x_i$. This will be further explained in the following.

Figure 3A:
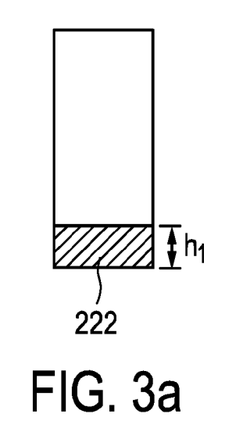
FIGS. 3*a* and 3*b* each show an exemplary bar graph of the ultrasound elastography system, when no lateral variation of axial motion is present.
Figure 3B:
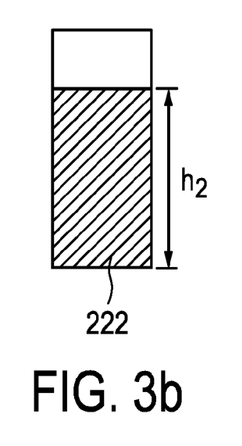

FIG. 3a and FIG. 3b each shows an exemplary bar graph 220 of the ultrasound elastography system 100, when no lateral variation of axial motion is present. For the examples of FIG. 3a and FIG. 3 b different degrees of average compression were applied. In each of FIG. 3a and FIG. 3b lateral variation of axial motion is not present and thus motion is purely axial motion. In this case, the shape of the bar 222 is rectangular, like a conventional bar graph. The heights $h_1$, $h_2$ of the bar 222 indicates a level of strain image quality. Additionally or alternatively, the color of the bar 222 can indicate the level of strain image quality (e.g. gray providing a low quality and green providing a high quality). The height $h_1$ of the bar 222 in FIG. 3a is smaller than the height $h_2$ of the bar 222 in FIG. 3b. The smaller height $h_1$ in FIG. 3a may indicate that the strain image quality level in FIG. 3a is lower than in FIG. 3b. Thus, in FIG. 3b a better quality strain image 200 would be provided compared to FIG. 3a.

Figure 4A:
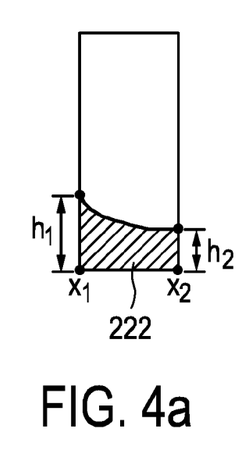
FIG. 4*a*-4*d* each shows an exemplary bar graph of the ultrasound elastography system, when lateral variation of axial motion is present.
Figure 4B:
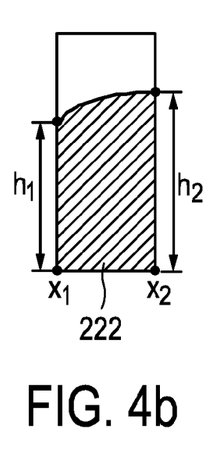
Figure 4C:
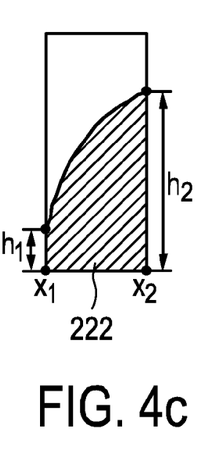
Figure 4D:
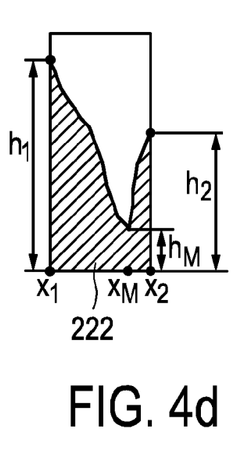

FIG. 4a to FIG. 4d each shows an exemplary bar graph 220 of the ultrasound elastography system 100, when lateral variation of axial motion is present. For the examples of FIG. 3a and FIG. 3 b various different degrees of average compression and tilting/rocking were applied. In each of FIG. 4a to FIG. 4d lateral variation of the axial motion is present. In this case, the shape of the bar 222 indicates the lateral variation of the strain image quality. In particular, the top side of the bar 222 indicates the lateral variation. In each of FIG. 4a to FIG. 4d the shape of the bar 222, in particular its top side, is slanted and curved as the strain image quality laterally varies. The shape of the bar 222 has at least two different heights $h_1$, $h_2$ at one point of time. In FIG. 4a the shape of the bar 222 decreases from a first lateral position $x_1$ having a first height $h_1$ to a second lateral position $x_2$ having a second height $h_2$ smaller than the first height $h_1$. In FIG. 4b the shape of the bar 222 increases from a first lateral position $x_1$ having a first height $h_1$ to a second lateral position $x_2$ having a second height $h_2$ bigger than the first height $h_1$. In FIG. 4c the shape of the bar 222 also increases from a first lateral position $x_1$ having a first height $h_1$ to a second lateral position $x_2$ having a second height $h_2$ bigger than the first height $h_1$. Compared to FIG. 4b, in FIG. 4c the shape of the bar 222 increases steeper. Thus, in FIG. 4c the difference between the first height $h_1$ and the second height $h_2$ is bigger as compared to FIG. 4b. In FIG. 4d the shape of the bar 222 is V-shaped. Thus, the shape of bar 222 decreases from a first lateral position $x_1$ having a first height $h_1$ to a medium lateral position $x_M$ (in between the first lateral position $x_1$ and the second lateral position $x_2$) having a medium height $h_M$, and increases from the medium lateral position $x_M$ to a second lateral position $x_2$ having a height $h_2$ bigger than the height $h_M$. The V-shape indicates that the axial motion changes direction in the lateral direction x with an intermediate lateral position $x_M$ having very little (e.g. close to zero) axial motion. This intermediate lateral position $x_M$ or region having nearly zero axial motion indicates or has poor or low strain image quality.

Figure 5A:
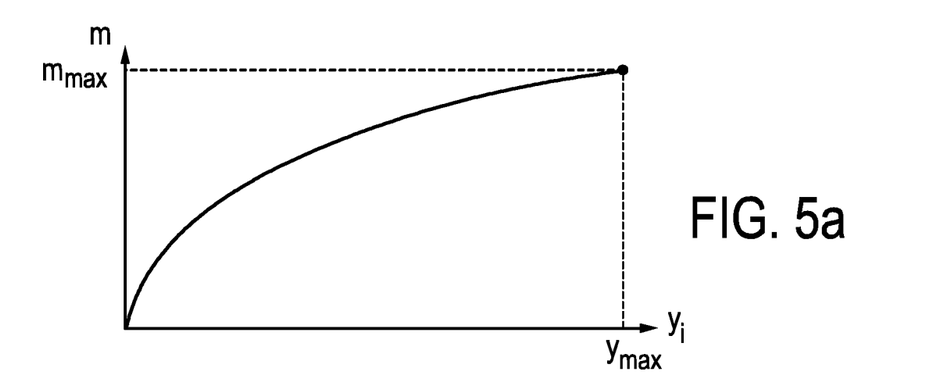
FIG. 5*a*-5*c* each shows an exemplary diagram of axial motion.
Figure 5B:
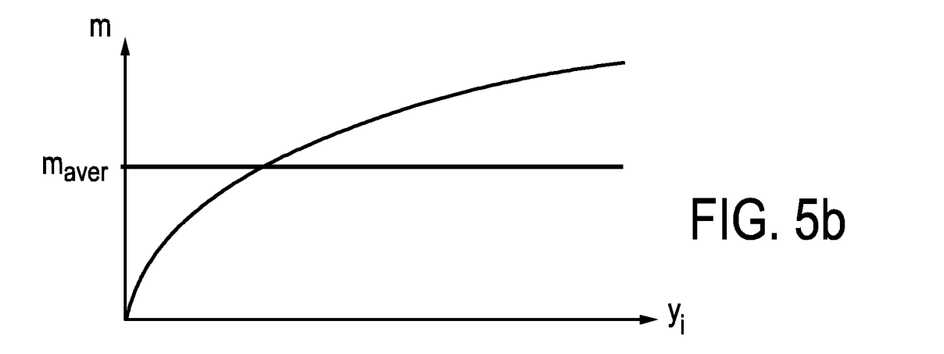
Figure 5C:
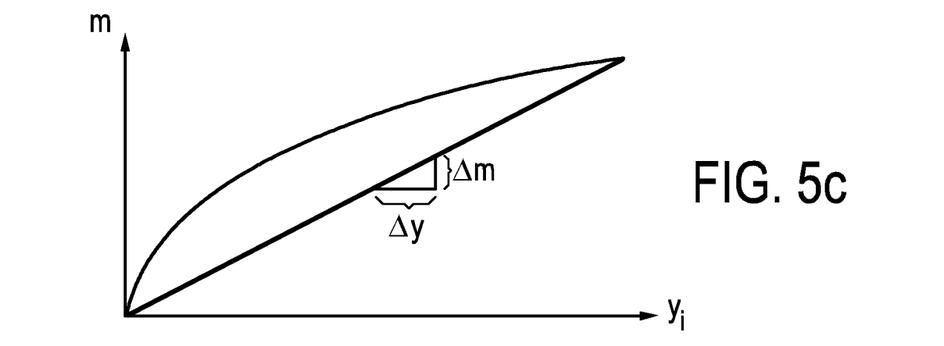

FIG. 5a to FIG. 5c each shows an exemplary diagram of axial motion. In each of FIG. 5a to FIG. 5c, for a specific lateral position $x_i$, an amount of relative axial motion m as a function of axial position $y_i$ is depicted. As can be seen in each of FIG. 5a to FIG. 5c axial motion m is a roughly monotonic function of axial position $y_i$ or depth.

In the first example of FIG. 5a a maximum amount $m_{max}$ of the amounts of relative axial motion m of the points of the plurality of points which have the respective lateral position $x_i$ is determined. In this case the axial motion data indicates the maximum amount $m_{max}$ of relative axial motion for each point $P(x_i, y_i)$ of two-dimensional data as explained with reference to FIG. 2a. In this example the maximum amount $m_{max}$ of axial motion as a function of lateral position $x_i$ is provided, which thus shows the lateral variation of axial motion.

In the second example of FIG. 5b the amount of axial motion of the points of the plurality of points which have the respective lateral position $x_i$ are averaged. This yields an average amount $m_{aver}$ of relative axial motion. In this case the axial motion data indicates the average amount $m_{aver}$ of relative axial motion for each point $P(x_i, y_i)$ of two-dimensional data as explained with reference to FIG. 2a. In this example the average axial motion $m_{aver}$ as a function of lateral position $x_i$ is provided, which thus shows the lateral variation of axial motion.

In the third example of FIG. 5c, the slope or derivative $\Delta m/\Delta y$ of the axial motion m indicates the strain. In FIG. 5c, the axial derivatives $\Delta m/\Delta y$ of the amounts of axial motion (thus the strains) of the points of the plurality of point which have the respective lateral position $x_i$ are averaged. This yields an average axial derivative $m'_{aver}$, thus average strain. In this case the axial motion data indicates the average strain for each point $P(x_i, y_i)$ of two-dimensional data as explained with reference to FIG. 2a. This averaging can for example be performed before the strain is normalized (auto-scaled) in the strain image data for displaying the strain image. In this example the average strains (derivatives of axial motion amounts) as a function of lateral position $x_i$ is provided, which thus shows the lateral variation of axial motion.

Figure 6A:
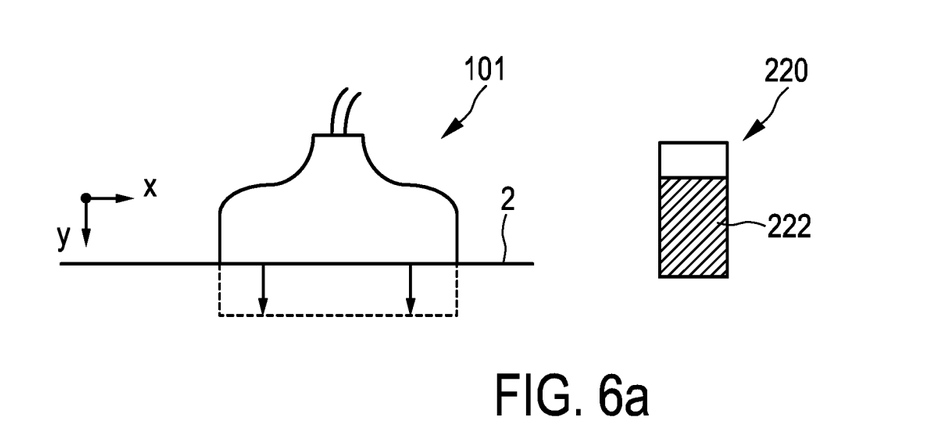
FIG. 6*a*-6*c* show three different examples of ultrasound probe motion and a corresponding bar graph.
Figure 6B:
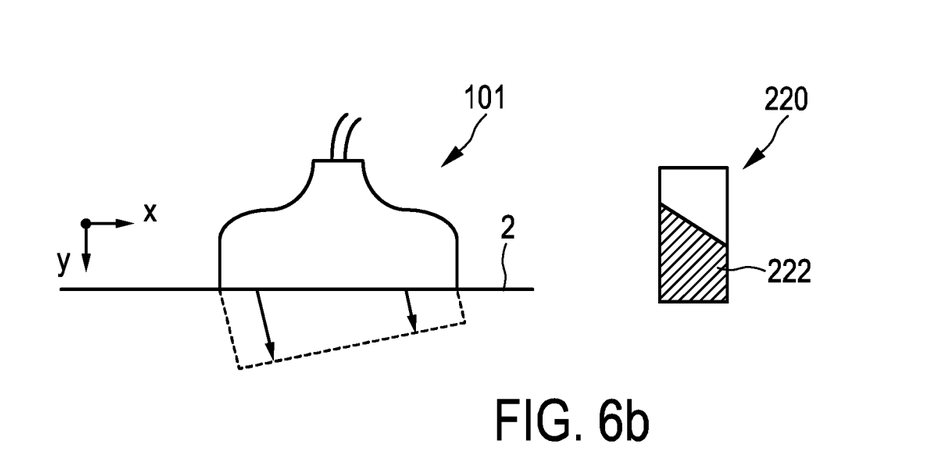
Figure 6C:
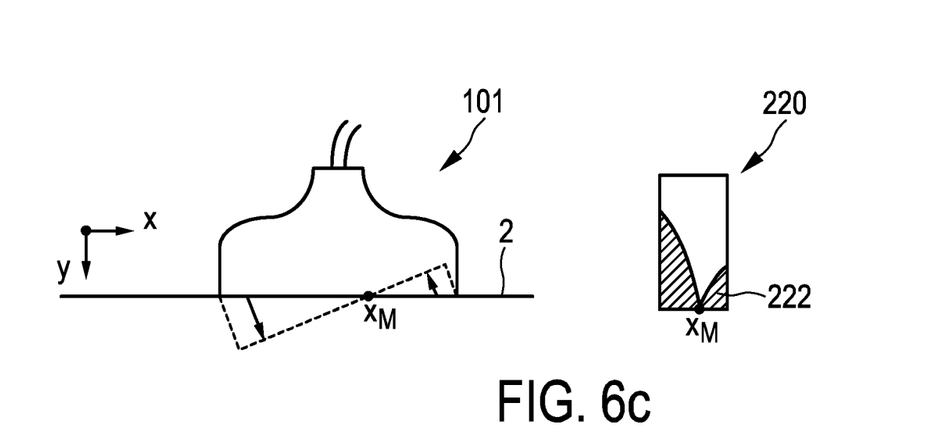

FIG. 6a-6c show three different examples of ultrasound probe motion and a corresponding bar graph 220. The ultrasound probe 101 is placed on a surface of a body, here skin 2 of a patient 1. In each of FIG. 6a-c the axial motion between the ultrasound probe 101 and the anatomical site of the patient 1 is indicated by arrows in the depth direction (y-direction). The motion indicated in FIG. 6a-c is exaggerated for illustration purposes. It should be noted that in reality the motion is in general extremely small compared to the size of the ultrasound probe 101, so that the change in the position or angle of the ultrasound probe 101 may not be noticeable by the user (e.g. using sight or touch). In the example of FIG. 6a lateral variation of axial motion is not present and thus motion is purely axial motion. The heights of the arrows (indicating the axial motion) are constant in the lateral direction (x-direction). In this case, the corresponding bar graph 220 has a rectangular shape of the bar 222 is rectangular, like a conventional bar graph (horizontal top side of bar 222). In the example of FIG. 6b lateral variation of axial motion (e.g. rocking and/or tilting) is present and thus there is a mixture of axial motion and lateral variation (e.g. rocking and/or tilting). The height arrows indicating axial motion are not constant, but varying in the lateral direction (x-direction). In this case, the corresponding bar graph 220 has a bar 222 which shape indicates the lateral variation of the strain image quality (slanted top side of bar 222). In the example of FIG. 6c, compared to the example of FIG. 6b, even more lateral variation (e.g. rocking and/or tilting) is present, such that the lateral variation of axial motion exceeds the axial motion. In this case, as indicated by the arrows in FIG. 6c, the axial motion changes direction in the lateral direction x (laterally across the image), with an intermediate point $x_M$ or region having nearly zero axial motion. In this case, the corresponding bar graph 220 has a V-shaped bar 222.

Figure 7:
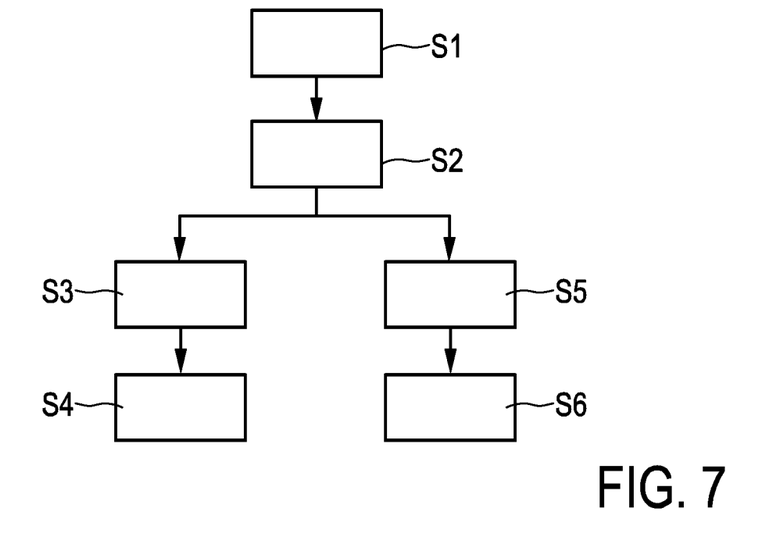
FIG. 7 shows a schematic block diagram of an ultrasound elastography method according to an embodiment.

FIG. 7 shows a schematic block diagram of an ultrasound elastography method according to an embodiment. In a first step Si a time-varying ultrasound signal is received from an ultrasound probe having at least one transducer element. The ultrasound probe can in particular be the ultrasound probe 101 as explained with reference to the embodiment of FIG. 1. In a further step S2 axial motion data based on the time-varying ultrasound signal is determined. The axial motion data indicates a relative axial motion between the ultrasound probe and the anatomical site in an axial direction y. In a further step S3 a lateral variation of the axial motion in a lateral direction x based on the actual motion data is determined. Further, in step S5 strain image data based on the axial motion data is determined. These determinations can for example be performed by a signal processing unit 103 as explained with reference to the embodiment of FIG. 1. In step S6 a strain image 200 of the anatomical site is displayed based on the strain image data. Further, in step S4 an indication of lateral variation of a quality of the strain image based on the lateral variation of the axial motion is displayed. These displaying steps can for example be performed by a display 105 as explained with reference to the embodiment of FIG. 1.

Figure 8:
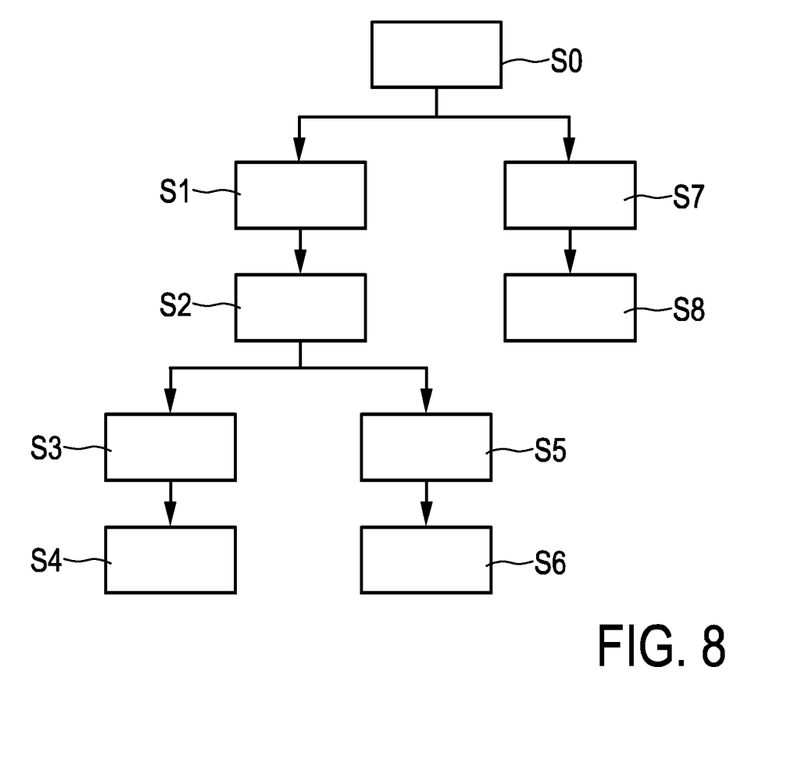
FIG. 8 shows a schematic block diagram of an ultrasound elastography method according to a variant of the embodiment of FIG. 7.

FIG. 8 shows a schematic block diagram of an ultrasound elastography method according to a variant of the embodiment of FIG. 7. The variant of FIG. 8 differs from the embodiment of FIG. 8 in an additional step S7 of determining ultrasound echo intensity data based on the ultrasound signal, and a step S8 of displaying an ultrasound echo intensity image of the anatomical site. The ultrasound echo intensity data and the strain data can be based on the ultrasound echo signal from the same transmit pulse (set of transmit pulses) or from different transmit pulses (sets of transmit pulses).

The explanation above has been made in connection with axial motion data being two-dimensional data for a plurality of points $P(x_i, y_i)$, each having an axial position $y_i$ and a lateral position $x_i$. However, it will be understood that the axial motion data can also be three-dimensional data for a plurality of points $P(x_i, y_i, z_i)$, each having an axial position $y_i$, a lateral position $x_i$ and an elevational position $z_i$. The signal processing unit 103 can then be configured to determine an elevational variation of the axial motion in an elevation direction z based on the axial motion data, and the display unit 105 can be configured to display an indication of elevational variation of strain image quality based on the elevational variation of the axial motion. The elevational direction z is orthogonal to each of the axial direction y and the lateral direction x. Further, the display unit can be configured to display a three-dimensional strain image or multi-planar strain image.

While the invention has been illustrated and described in detail in the drawings and foregoing description, such illustration and description are to be considered illustrative or exemplary and not restrictive; the invention is not limited to the disclosed embodiments.

Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

A computer program may be stored/distributed on a suitable medium, such as an optical storage medium or a solid-state medium supplied together with or as part of other

The invention claimed is:

1. An ultrasound elastography system for providing a strain image of an anatomical site, the system comprising:
   an ultrasound probe including at least one transducer element;
   a signal processing circuit communicatively coupled to the ultrasound probe and configured to:
      receive a time-varying ultrasound signal from the ultrasound probe,
   determine axial motion data based on the time-varying ultrasound signal, the axial motion data indicating a relative axial motion between the ultrasound probe and the anatomical site in an axial direction, and determine a lateral variation of the relative axial motion in a lateral direction by determining, for at least two lateral positions in the lateral direction, an amount of the relative axial motion and by comparing the amounts of the relative axial motion; and
   a display unit communicatively coupled to the signal processing unit that configures the display to:
      display a strain image of the anatomical site based on strain image data which is determined based on the axial motion data, and display an indication of a lateral variation of a quality of the strain image by displaying the amounts of the relative axial motion as a function of lateral position on a bar graph comprising a bar, wherein a shape of a top side of the bar indicates the lateral variation of the quality of the strain image and a height of the bar indicates a level of the quality of the strain image.

2. The system of claim 1, wherein the axial motion data is two-dimensional data for a plurality of points each having an axial position and a lateral positon.

3. The system of claim 2, wherein the determining the amount of the relative axial motion comprises averaging the amounts of the relative axial motion of points of the plurality of points which share the lateral position.

4. The system of claim 2, wherein the determining the amount of the relative axial motion comprises averaging axial derivatives of the amounts of the relative axial motion of points of the plurality of points which share the lateral position.

5. The system of claim 1, wherein the shape of the top side of the bar is slanted and/or curved when the quality of the strain image laterally varies.

6. The system of claim 1, wherein the system is configured to display the indication of the lateral variation of the quality of the strain image in real-time and/or store the indication of the lateral variation of the quality of the strain image in a non-transitory memory for later displaying.

7. The system of claim 1, wherein the display unit is further configured to display an ultrasound echo intensity image of the anatomical site.

8. The system of claim 1, wherein the signal processing circuit is further configured to determine an elevational variation of the relative axial motion in an elevation direction based on the axial motion data, and the display unit is configured to additionally display an indication of an elevational variation of the quality of the strain image based on the elevational variation of the relative axial motion.

9. An ultrasound elastography method for providing a strain image of an anatomical site, the method comprising:
   receiving a time-varying ultrasound signal from an ultrasound probe having at least one transducer element;
   determining axial motion data based on the time-varying ultrasound signal, the axial motion data indicating a relative axial motion between the ultrasound probe and the anatomical site in an axial direction;
   determining a lateral variation of the relative axial motion in a lateral direction based on the axial motion data by determining, for at least two lateral positions in the lateral direction, an amount of the relative axial motion and by comparing the amounts of the relative axial motion;
   displaying a strain image of the anatomical site based on strain image data that is determined based on the axial motion data;
   displaying an indication of lateral variation of a quality of the strain image based on the lateral variation of the relative axial motion by displaying the amounts of the relative axial motion as a function lateral position on a bar graph comprising a bar; wherein
   a shape of a top side of the bar indicates the lateral variation of the quality of the strain image and a height of the bar indicates a level of the quality of the strain image.

10. A non-transitory computer readable media comprising computer program code executable by a computer to cause the computer to carry out the steps of the method as claimed in claim 9.

* * * * *